US00PP33166P2

(12) United States Plant Patent
Hansen

(10) Patent No.: US PP33,166 P2
(45) Date of Patent: Jun. 15, 2021

(54) **X *MANGAVE* PLANT NAMED 'FIERCELY FABULOUS'**

(50) Latin Name: ***Manfreda* x *Agave* hybrid**
Varietal Denomination: Fiercely Fabulous

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/974,233

(22) Filed: Nov. 19, 2020

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
CPC ... A01H 5/12; A01H 5/02; A01H 5/00; A01H 6/12; A01H 1/02
See application file for complete search history.

*Primary Examiner* — June Hwu

(57) ABSTRACT

A new and unique X *Mangave* plant named 'Fiercely Fabulous' characterized by compact habit of lanceolate foliage with medium grayish-green color and grayed-purplish spots and burgundy air-brushing with strong ultraviolet light exposure. The new plant has numerous chartreuse flowers with burgundy blushing on tall, stiff, highly-branched scapes. The new plant is suitable as a potted houseplant plant, as a container plant for the patio or garden and for the garden or planted in the landscape, and the flowers are loaded with nectar for attracting hummingbirds.

2 Drawing Sheets

Botanical classification: *Manfreda* x *Agave* hybrid.
Variety denomination: 'Fiercely Fabulous'.

STATEMENT REGARDING PRIOR DISCLOSURES UNDER 37 CFR 1.77(b)(6)

The first non-enabling public disclosure of X *Mangave* 'Fiercely Fabulous' was on Mar. 2, 2020 as a brief description and photo on two websites operated by Walters Gardens, Inc. Information for this website and plants for this sale were obtained from the inventor. No plants of X *Mangave* 'Fiercely Fabulous' have been sold, in this country or anywhere in the world, nor has any disclosure of the new plant been made, more than one year prior the filing date of this application, and such disclosure within one year was either derived directly or indirectly from the inventor.

BACKGROUND OF THE INVENTION

The present invention relates to the new and distinct X *Mangave* plant, X *Mangave* 'Fiercely Fabulous' hybridized on Nov. 20, 2015 by the inventor at a wholesale perennial nursery in Zeeland, Mich., USA as a cross between an unreleased proprietary hybrid X *Mangave* known by the breeder code 12-3-31 as the female or seed parent and an unreleased proprietary hybrid X *Mangave* known by the breeder code 12-11-2 as the male or pollen parent. Through trials at the same nursery the plant was referred to by the code 16-22-12. The new plant has been successfully asexually propagated initially in 2018 by shoot tip tissue culture at the same nursery in Zeeland, Mich. This asexual propagation system has been found to produce stable and identical plants that maintain all the unique characteristics of the original plant in successive generations.

BRIEF SUMMARY OF THE INVENTION

X *Mangave* 'Fiercely Fabulous' differs from its parents as well as all other *Manfreda, Agave* and X *Mangave* known to the applicant. The most similar known X *Mangave* cultivar known to the inventor are: 'Silver Fox' U.S. Plant Pat. No. 29,642, 'Mayan Queen' U.S. Plant Pat. No. 31,312, 'Catch a Wave' U.S. Plant Pat. No. 29,723, 'Moonglow' U.S. Plant Pat. No. 29,195, 'Aztec King' U.S. Plant Pat. No. 32,151, 'Desert Dragon' U.S. Plant Pat. No. 31,311, 'Inkblot' U.S. Plant Pat. No. 29,431, and 'Freckles and Speckles U.S. Pat. No. 30,904.

'Silver Fox' has a more compact habit and lacks the grey-purple spotting. 'Mayan Queen' lacks the grey-purple spotting. 'Catch a Wave' has leaves that are a more silvery-blue coloration and the leaves are more folded. 'Moonglow' has narrower leaves that lack the large teeth, and the habit is flatter. 'Aztec King' has broader leaves on a larger habit and lacks the large marginal teeth. 'Desert Dragon' has narrower leaves with a more undulating margin and lacks the large marginal teeth. 'Inkblot' has flatter growth habit, the leaves arch more, are longer, thinner and narrower, with less burgundy airbrushing, and the marginal teeth are smaller. 'Freckles and Speckles' has narrower, shorter foliage with smaller spotting, lacks the large marginal teeth, and has a smaller, less arching habit.

The female parent has bright yellow flowers on heavier branched scapes and the foliage lacks the greyed-purple spotting of the new plant. The male parent has wider leaves with greyed-purple spotting and the habit of the foliage is more upright.

The new plant, 'Fiercely Fabulous', is unique from all of these variegated *Agave*, X *Mangave* and *Manfreda* known to the inventor by the following combined traits:

1. Compact mounded habit with 30 to 40 leaves at flowering;
2. About with 30 to 40 lanceolate leaves at flowering;
3. Foliage with large flexible marginal teeth and semi-flexible sharp apical mucro;

4. Leaves develop grayed-purplish spots and burgundy air brushing with strong ultraviolet light exposure;
5. Moderate to rapid growth rate;
6. Numerous flowers of chartreuse with burgundy blushing on stiff, tall, highly-branched scapes.

BRIEF DESCRIPTION OF THE DRAWINGS

The photograph of the new plant demonstrates the overall appearance of the new plant including the unique traits as a three-year-old plant grown in a full-sun trial garden with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
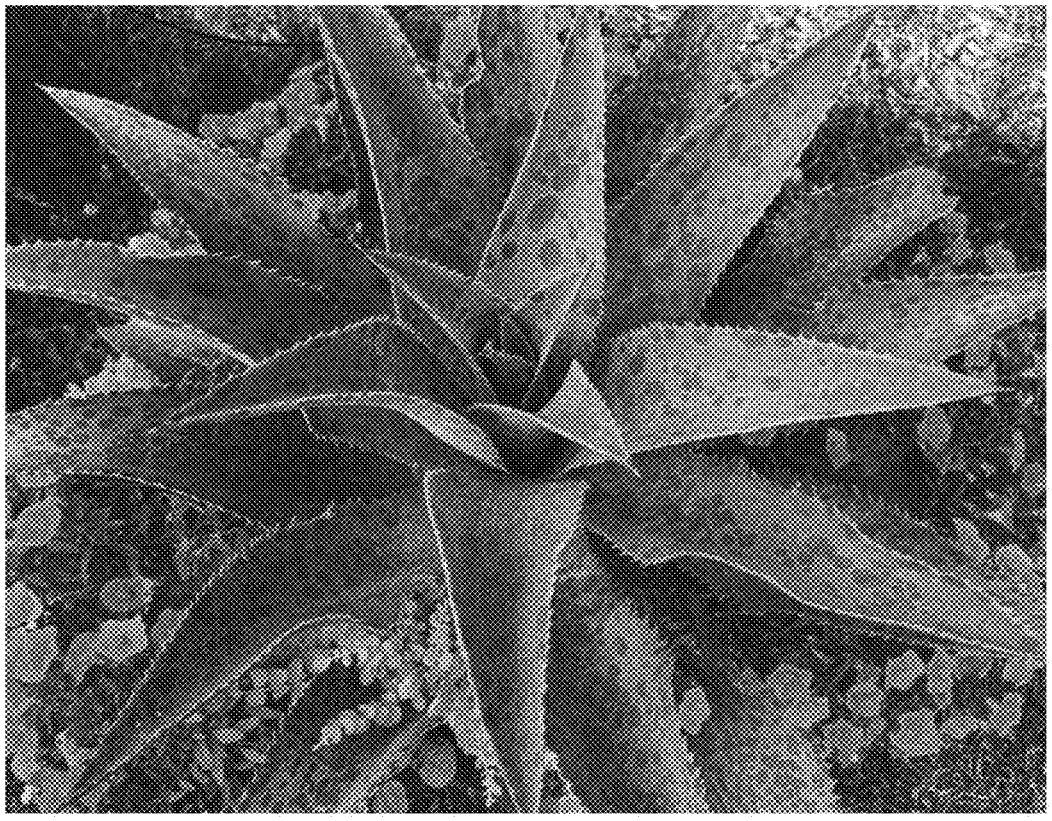
FIG. 1 shows the new plant from above.
Figure 2:
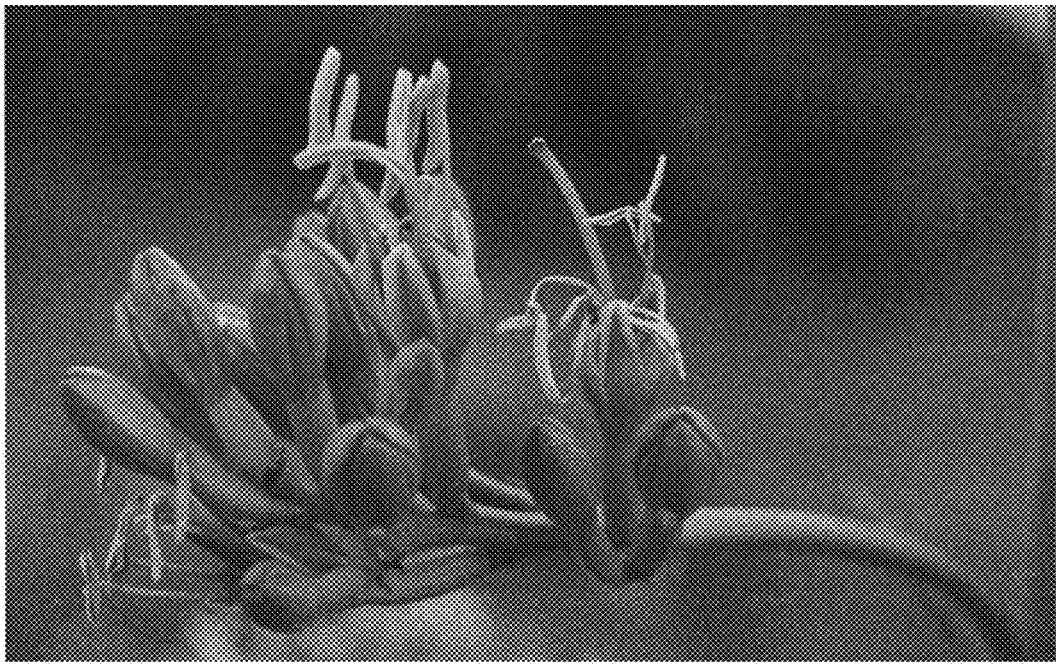
FIG. 2 shows a close-up of the flowers and buds in the upper scape.
Figure 3:
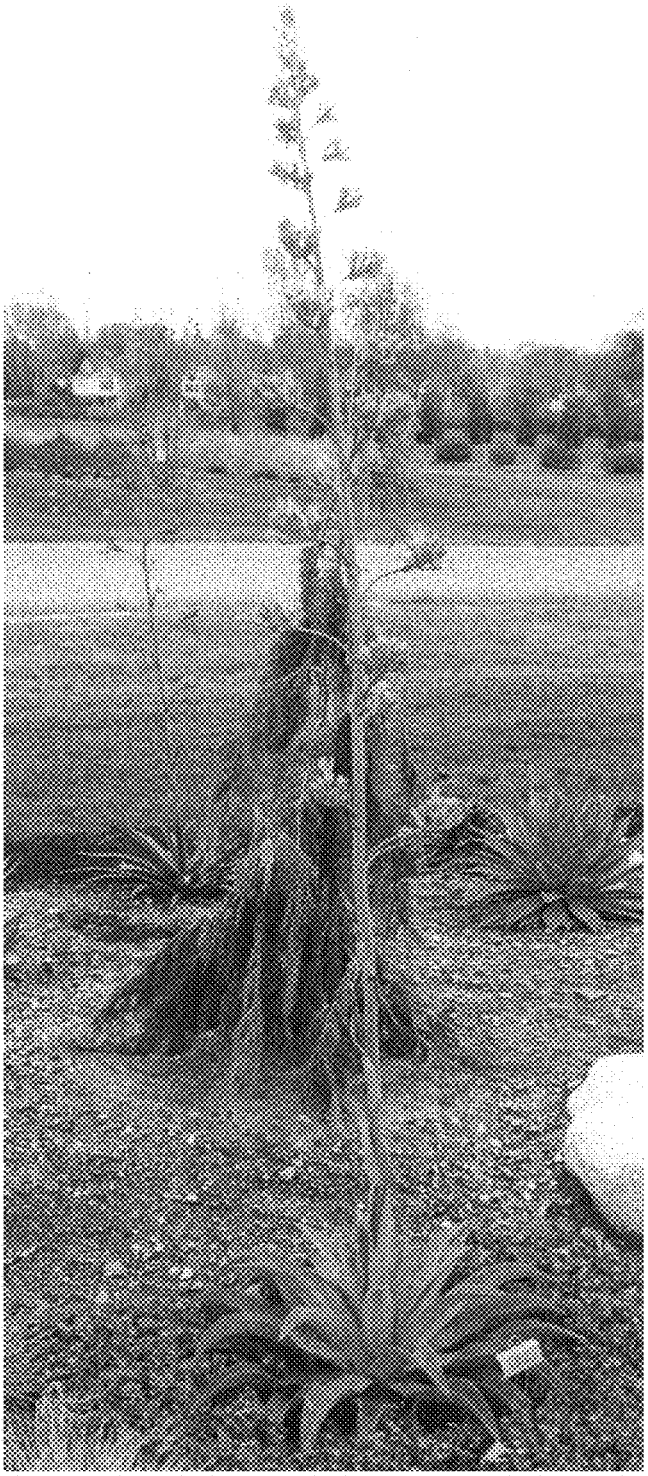
FIG. 3 shows the foliage habit and scape of the new plant in early flower development.

The following descriptions and color references are based on the 2015 edition of The Royal Horticultural Society Colour Chart except where common dictionary terms are used. The new plant, X *Mangave* 'Fiercely Fabulous', has not been observed under all possible environments. The phenotype may vary slightly with different environmental conditions, such as temperature, light, fertility, moisture and maturity levels, but without any change in the genotype. The following observations and size descriptions are of two and three-year old plants in a commercial wholesale greenhouse in Zeeland, Mich. with supplemental water and fertilizer as needed.

Botanical classification: X *Mangave* hybrid (*Manfreda* x *Agave*);

Parentage: 12-3-31 as the female or seed parent and 12-11-2 as the male or pollen parent;

Propagation: Division and sterile plant tissue culture;

Time to initiate roots from tissue culture: About 21 days;

Growth rate: Moderate to rapid;

Crop time: About 12 to 16 weeks to finish during lengthening spring days from an established 25 mm tissue culture plug to a 65 mm diameter container;

Rooting habit: Fleshy, lightly branching, with roots up to 30 cm long;

Root color: Nearest RHS 158C;

Plant shape and habit: Succulent herbaceous perennial with basal rosettes of up to about 38 fleshy leaves radially emerging and arching from central rhizome, producing a symmetrical, low, rounded mound;

Plant size: Foliage height about 25.0 cm tall from soil line to the top of the leaves and 67.0 cm wide at soil level, flowering to about 218.0 cm tall and to about 33.0 cm wide at the widest flowers;

Foliage description: Lanceolate; simple; sarcous; glabrous; fibrous; slightly asperous and glaucous adaxial and abaxial; margins coarsely dentate with flexible teeth; apex acute with sharp semi-flexible mucro; base truncate, sessile, clasping; concavo-convex and slightly sinuate with maturity;

Leaf size: To about 33.0 cm long, about 8.5 cm wide at middle, 5.8 cm wide at base, 1.5 cm thick and 3.0 cm deep; average about 29.5 cm long, 6.5 cm wide in middle, 4.5 cm wide at base and 1.0 cm thick; usually bi-laterally symmetrical; glabrous and slightly glaucous above and below; speckles of variable sizes from about 1.5 mm diameter to about 13.0 mm long and 8.0 mm across, frequently overlapping; teeth to about 5.0 mm long and 5.0 mm across at base;

Foliage fragrance: None observed;

Leaf blade color:

*Adaxial* (*young*).—Nearest RHS 147C with speckles nearest RHS 191A.

*Abaxial* (*young*).—Nearest RHS 138B with speckles nearest RHS N187A.

*Adaxial* (*mature*).—Blend between RHS N138C and RHS 188B, maculate with speckles of between RHS N186C and RHS N187B and with higher ultraviolet moderately blushed nearest RHS N186C.

*Abaxial* (*mature*).—Between RHS 189B and RHS 191B, with speckles of nearest RHS N187B.

*Marginal teeth.*—Adaxial and abaxial base between RHS N187B and RHS 191A; adaxial distal 2.0 mm tip nearest RHS 161C and abaxial 2.0 mm tip nearest RHS 161C on older leaves; and younger adaxial and abaxial leaves nearest RHS 156D in distal 1.5 mm tips.

Mucro: Semi-flexible; sharp; straight, about 9.0 mm long and 1.2 mm across;

Mucro color: Nearest RHS 200A;

Petiole: Sessile;

Veins: Parallel; not distinct;

Peduncle: Terete; glaucous; glabrous; stiff; strong; upwardly; heavily branched with about 38 branches; about 218.0 cm long and 2.5 cm diameter at base and 2.0 cm diameter below first branches; branches to about 17.0 cm long and about 0.7 cm diameter at base; branch aspect upwardly and outwardly distally becoming more outwardly;

Peduncle color: Proximally between RHS N186C and RHS N187B, distally nearest RHS 147C with blush nearest RHS N186C diminishing to RHS 146C in distal 15 cm; branches nearest RHS N186C in proximal region with reduced blushing distally to RHS 146C without blushing;

Pedicel: Terete; glaucous; glabrous; stiff; strong; average about 1.5 mm long and 3.0 mm diameter;

Pedicel color: Nearest RHS 146D;

Cauline bracts: About 14 per scape below flowers and one at each branch; lanceolate; simple; sarcous, glabrous; margins finely dentate with flexible teeth to about 0.5 mm long; apex narrowly acute with semi-flexible mucro to about 4 mm long; base truncate, sessile, clasping; typically adpressed in proximal two-thirds; to about 19.0 cm long and about 3.0 cm wide near base, decreasing distally; color adaxial nearest RHS 147C where adpressed to stem and developing light blush and spots of nearest RHS N186C where exposed to more sun, abaxial between RHS 138C and 147C where overlapped with other bracts and where exposed to more sun between RHS 147C with moderate blush of N186C and spots of nearest RHS N187B;

Buds one day prior to opening: Elongated globose; about 3.8 cm long and about 10.0 mm across at bulb, base about 5.0 mm diameter, bulb about 2.2 cm long;

Bud color: Nearest RHS 146D in basal portion and distally becoming between RHS 178B and RHS 183B;

Flower description: Perfect; incomplete; actinomorphic; about 5.6 cm long to exserted anthers and pistil and opening to about 3.0 cm across at outside of anthers;

corolla to about 2.7 cm long and 1.8 cm wide at apex; lasting about 3 to 4 days per flower; flowering period about three weeks once plant is mature, approximately three-years-old; producing abundant nectar;

Inflorescence: Approximately 450 to 500 flowers per scape; aspect mostly upright; flowering portion about 148.0 cm tall and about 30.0 cm across;

Flower fragrance: None detected;

Tepals: Six in two sets of three; glabrous and slightly lustrous adaxial and abaxial; acute apex and fused base; outer set about 25.0 mm long, fused in basal 10.0 mm and about 6.0 mm wide just above fusion; inner set about 25.0 mm long and 7.0 mm wide just above fusion; inner set creased on abaxial side along margin where overlapped with outer set while in bud;

Tepal color: Outer tepal set adaxial base between RHS 151A and RHS 153D, middle portion nearest RHS 153D, distally becoming more concentrated maculate with nearest RHS 183A with undertone of RHS 163B; outer set abaxial base between RHS 151A and RHS 153D, middle portion nearest RHS 153D with light blush nearest RHS 187B, distally becoming more concentrated to nearly solid RHS 183A; inner tepal set adaxial base between RHS 151A and RHS 153D, middle portion longitudinal center between RHS 146D and RHS N144D with margins nearest RHS 162B with light blush nearest RHS 183A; abaxial inner set base nearest RHS 146D, middle portion margin lighter than RHS 153D and longitudinal center between RHS 146D and RHS 160B moderately blushed with RHS 187B;

Androecium: Six;

*Filaments.*—Six; terete distally, slightly applanate base; stiff and straight; about 30.0 mm long and 1.0 mm across at base; adnate with inner corolla in proximal 5.0 mm; color nearest RHS 162A and moderately maculate with nearest RHS 187C.

*Anther.*—Dorsifixed; longitudinal; straight, oblong; about 16.0 mm long and 2.0 mm diameter before opening; color nearest blend between RHS 151B and RHS 160A.

*Pollen.*—Abundant; color nearest RHS 9A.

Gynoecium: Single; 54.0 mm long;

*Style.*—34.0 mm long and 2.0 mm diameter at base; color at base nearest RHS 160D, distally between RHS 144D and RHS 146D and moderately maculate in the middle portion with nearest RHS 187C.

*Stigma.*—Turbinate, apex tri-lobed; distally puberulent; about 2.5 mm tall and 3.0 mm across top; color side nearest RHS N199B; top stigmatic surface in tri-pointed star with color nearest RHS 196C.

*Ovary.*—Inferior; oblong; about 18.0 mm long and 5.0 mm across; surface smooth; color nearest RHS 146D.

Fruit: Not yet observed;

Seed: Not yet observed;

Disease resistance: X *Mangave* 'Fiercely Fabulous' has not been observed to be resistant to diseases common to other X *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'Fiercely Fabulous' as herein described and illustrated.

* * * * *